(12) United States Patent
Ratner

(10) Patent No.: US 10,539,485 B1
(45) Date of Patent: Jan. 21, 2020

(54) DEVICE AND METHOD FOR COLLECTING LYMPH NODES FROM FATTY TISSUE

(71) Applicant: Oleg Ratner, San Diego, CA (US)

(72) Inventor: Oleg Ratner, San Diego, CA (US)

( * ) Notice: Subject to any disclaimer, the term of this patent is extended or adjusted under 35 U.S.C. 154(b) by 0 days.

(21) Appl. No.: 16/221,245

(22) Filed: Dec. 14, 2018

Related U.S. Application Data

(60) Provisional application No. 62/744,029, filed on Oct. 10, 2018.

(51) Int. Cl.
G01N 1/00 (2006.01)
G01N 1/06 (2006.01)
G01N 33/483 (2006.01)
G01N 1/31 (2006.01)

(52) U.S. Cl.
CPC ............. *G01N 1/06* (2013.01); *G01N 1/312* (2013.01); *G01N 33/4833* (2013.01); *A61M 2202/08* (2013.01); *G01N 2001/065* (2013.01)

(58) Field of Classification Search
CPC ...................................................... G01N 1/00
See application file for complete search history.

(56) References Cited

U.S. PATENT DOCUMENTS

| 1,952,523 | A | * | 3/1934 | Abbott | G01N 3/14 |
| --- | --- | --- | --- | --- | --- |
| | | | | | 73/795 |
| 5,096,676 | A | | 3/1992 | McPherson et al. | |
| 5,127,537 | A | | 7/1992 | Graham | |
| 5,130,105 | A | | 7/1992 | Carter et al. | |
| D340,117 | S | | 10/1993 | Smalley et al. | |
| D349,773 | S | | 8/1994 | Malin et al. | |
| 5,427,742 | A | | 6/1995 | Holland | |
| 5,484,731 | A | | 1/1996 | Stevens | |
| 5,827,217 | A | | 10/1998 | Silver et al. | |
| D421,498 | S | | 3/2000 | Livingston | |
| D461,554 | S | | 8/2002 | Lafond et al. | |
| D694,085 | S | | 11/2013 | Fukano et al. | |
| D716,627 | S | | 11/2014 | Lin | |
| D760,053 | S | | 6/2016 | Schweigert | |
| D775,830 | S | | 1/2017 | Curver | |
| 10,126,215 | B2 | | 11/2018 | Stern et al. | |
| 2007/0225665 | A1 | * | 9/2007 | Perez-Cruet | A61F 2/4644 |
| | | | | | 604/317 |

OTHER PUBLICATIONS

"Hamstring Harvesting Instrument Case" <https://www.arthrex.com/products/AR-1279C> date unknown.

* cited by examiner

Primary Examiner — Jyoti Nagpaul
(74) Attorney, Agent, or Firm — Wagenknecht IP Law Group PC

(57) ABSTRACT

Devices and methods for yielding lymph nodes from fatty tissue, the device including a fenestrated sample chamber configured to receive a sample of fatty tissue having lymph nodes; a lockable gate switchable between a closed position that is locked and an open position; a pusher configured to push the sample against the gate when locked in the closed position to compress the tissue, and configured to push the compressed tissue out of the sample chamber when the gate is subsequently opened; and a cutting chamber aligned distal to the sample chamber for receiving compressed tissue from the sample chamber, the cutting chamber comprising sets of opposing through slots aligned to permit slicing of the compressed tissue into sections, thereby yielding lymph nodes from the fatty tissue.

18 Claims, 8 Drawing Sheets

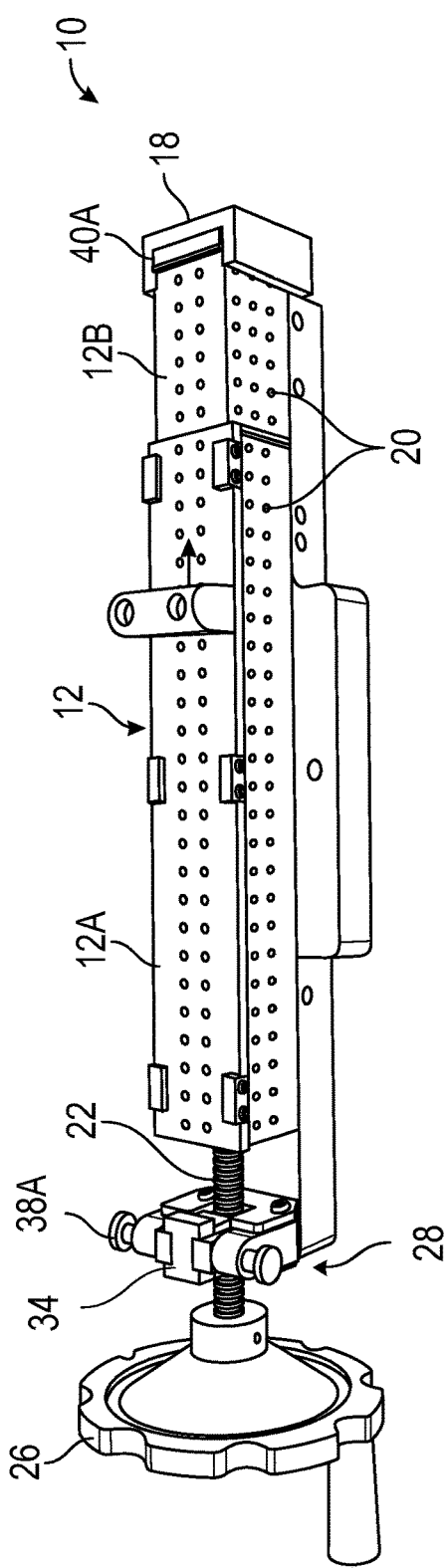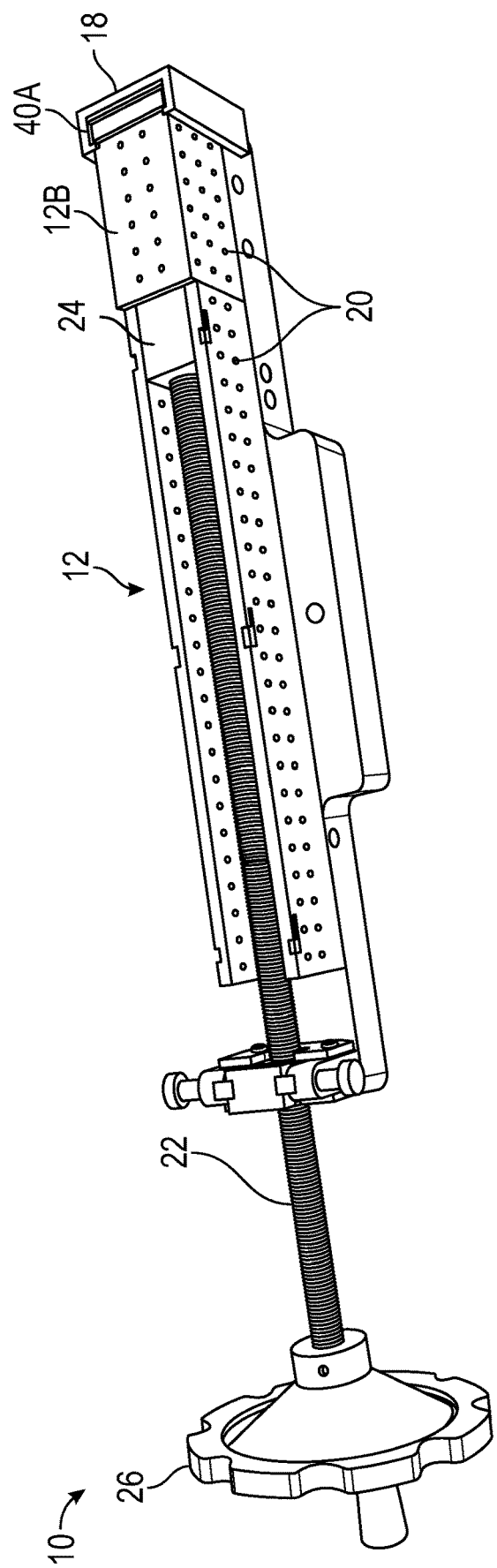

DEVICE AND METHOD FOR COLLECTING LYMPH NODES FROM FATTY TISSUE

CROSS REFERENCE TO RELATED APPLICATIONS

This application claims benefit of priority to U.S. provisional patent application No. 62/744,029, filed Oct. 10, 2018; the content of which is herein incorporated by reference in its entirety.

TECHNICAL FIELD

The invention relates generally to the field of medical devices and more specifically to a device for yielding lymph nodes from fatty tissue, which presents the lymph nodes in densely packed tissue sections for histopathological evaluation and improved staging of cancerous conditions.

BACKGROUND OF THE INVENTION

The metastatic involvement of lymph nodes is a determining factor for staging various cancers. Although evaluation of all resected material including all lymph nodes and all surrounding biological components having useful information (referred to as "total embedded material") would be preferred, it is not feasible using conventional techniques because it would require processing hundreds of histology cassettes, many of which would not include any lymph nodes or useful information. Therefore, current approaches focus on identifying and removing lymph nodes from resected fatty tissue. However, there is disagreement as to how many lymph nodes should be evaluated for effective staging. Clinical quality guidelines suggest the evaluation of at least 12 lymph nodes; however, there is increasing acceptance that evaluation of 12 lymph nodes is insufficient for adequate staging. Studies have found that, particularly in patients at stages I-II colon cancer, there is a direct proportional relationship between the number of lymph nodes evaluated and rate of survival.

There are different variables that affect the retrieval of lymph nodes. Among these include effectiveness of the surgeon, the surgery and the pathology exam. Ideally, the surgeon should remove all original lymph nodes pertaining to a tumor, and the pathologist should sample and examine them thoroughly. However, retrieving lymph nodes from resected fatty tissue is time consuming and requires additional training of personnel.

Lymph nodes are conventionally retrieved from fatty tissue using manual palpation with the fingers. To this end, lymph nodes that are more visible and palpable tend to be collected at a higher frequency than those that are smaller. However, some studies suggest that 45%-78% of metastatic lymph nodes have a diameter less than 5 mm, and some metastatic lymph nodes have a diameter even less than 1 mm. As should become apparent, manual palpation is not only laborious but is also prone to error. Studies show that manual palpation methods at best achieve about 50% of lymph nodes from a resected fatty tissue sample, which correlates to a false negative error of 10-35%.

Due to both the importance and challenges associated with retrieving lymph nodes sized at only a few millimeters or less, it has been suggested that fat clearance techniques or the intra-arterial injection of methylene blue may improve identification and retrieval methods; however, even in such instances the staff must work through the entire fatty tissue sample manually to obtain the maximum number of indentifiable lymph nodes, which is usually limited to those sized about 5 mm or greater.

Accordingly, there remains a need to improve the yield of lymph nodes from fatty tissue for histopathological evaluation. Further, there remains a need to decrease the time requirement and skill level required to achieve these higher yields.

SUMMARY OF THE INVENTION

The invention addresses the above challenges and provides related benefits. In particular, the devices and methods significantly increase the yield of lymph nodes for histopathological evaluation compared to manual palpation methods. The device and methods can yield 100% of lymph nodes from resected fatty tissue. Further, the devices and methods provide an alternative approach to manual palpation of fatty tissue with the finger tips. Still further, the devices and methods produce a dense block of tissue containing total embedded material, which is substantially free of fat cells. This total embedded material includes lymph nodes, arteries, veins, nerves and connective tissue for histopathological evaluation, which can provide information regarding the staging of cancer. Due to the high tissue density, the evaluation of not only all lymph nodes but total embedded material can be performed using fewer histology cassettes compared to conventional methods.

The above is accomplished in a first aspect of the invention by way of a device for yielding lymph nodes from fatty tissue. The device includes a fenestrated sample chamber configured to receive a sample of fatty tissue having lymph nodes; a lockable gate switchable between a closed position that is locked and an open position; a pusher configured to push the sample against the gate when locked in the closed position to compress the tissue, and configured to push the compressed tissue out of the sample chamber when the gate is subsequently opened; and a cutting chamber aligned distal to the sample chamber for receiving the compressed tissue from the sample chamber, the cutting chamber having sets of opposing through slots aligned to permit slicing of the compressed tissue into sections, thereby yielding the lymph nodes from the fatty tissue, such as for histopathological evaluation.

The sample chamber is preferably formed with a fixed top portion positioned distal to a removable top portion. The removable top portion permits repeated sample loading after compressing tissue under the fixed top portion.

In some embodiments, the sample chamber and cutting chamber have complementary structures that reversibly attach to one another, thereby permitting the cutting chamber to reversibly connect to the sample chamber. In other embodiments, the sample chamber and cutting chamber are integral with one another.

In some embodiments, the pusher includes a block and a threaded rod. A guide is preferably positioned proximal to the sample chamber to longitudinally guide the rod through the sample chamber. In some embodiments, the guide has a removable threaded top that is threaded along its interior, while the interior of the guide along the bottom and sides is not threaded. In such embodiments, the guide can include complimentary structures that lock and unlock the threaded top for attachment and removal, thereby providing two different configurations, namely, an attached configuration for helical movement of the rod along the threaded top and a removed configuration for longitudinally sliding the rod along the bottom and optionally inner sides.

The device can also include a base onto which the sample chamber reversibly locks. The guide can upwardly extend from the base and can be attachable to the base or integral with the base.

The lockable gate can be an end cap that reversibly caps the distal end of the sample chamber when the cutting chamber is not connected. When locked, the gate provides a distal surface against which the tissue can be compressed. Then, opening the gate permits the compressed tissue to be pushed distally out of the sample chamber and thus into the cutting chamber.

The device can also include a moveable support that fits within a pair of opposing through slots to traverse the cutting chamber and can include a spatula sized for insertion into the cutting chamber to assist with removing sections of compressed tissue.

In a related aspect of the invention, a method of sectioning tissue into sections for histology cassettes is provided. The method includes providing the device for yielding lymph nodes from fatty tissue; adding fatty tissue having lymph nodes to the sample chamber; locking the gate in the closed position; pushing the fatty tissue against the gate to compress the tissue; opening the gate; pushing the compressed tissue between the sets of opposing through slots; and cutting the compressed tissue through the sets of opposing through slots, to form a plurality of compressed tissue sections sized for placement in histology cassettes. The method also includes pretreating the fatty tissue with a solvent that at least partially dissolves fatty tissue for elution (wash-out). Preferably most of the fatty tissue is dissolved. Most preferably, all or nearly all of the fatty tissue is dissolved. The method can also include before the step of cutting the tissue, positioning a support across a set of opposing through slots of the cutting chamber and abutting a distal end of the compressed tissue, thereby providing a distal support for the compressed tissue during cutting.

In another related aspect of the invention, a device for yielding lymph nodes from fatty tissue is provided, which includes a fenestrated sample chamber configured to receive a sample of fatty tissue having lymph nodes; a lockable gate switchable between a closed position that is locked and an open position; a pusher configured to push the sample against the gate when locked in the closed position to compress the tissue, and configured to push the compressed tissue out of the sample chamber when the gate is subsequently opened; and a wheel spaced distal to the sample chamber to form a cutting space and configured for rotation around a longitudinal axis of the sample chamber, the wheel having one, two, three, four or more receiving ports rotationally aligned to receive the compressed tissue from the sample chamber in series. In preferred embodiments, the wheel includes at least three or four ports.

In still another related aspect of the invention, a method of sectioning tissue into uniform sections for histology cassettes is provided, which includes providing the above device for yielding lymph nodes from fatty tissue; adding a sample of fatty tissue having lymph nodes to the sample chamber; locking the gate in the closed position; pushing the fatty tissue against the gate to compress the tissue; opening the gate; pushing the compressed tissue into a first receiving port using the pusher; cutting the compressed tissue within the cutting space to form a tissue section sized for placement in a histology cassette; rotating the wheel to align a second receiving port with the sample chamber; pushing the compressed tissue into the second receiving port using the pusher; cutting the compressed tissue within the cutting space to form a second tissue section sized for placement in a histology cassette; and optionally removing the cut tissue sections from the wheel at any point.

BRIEF DESCRIPTION OF THE DRAWINGS

Embodiments of the invention can be better understood with reference to the following drawings, which form part of the specification and represent preferred embodiments. The features presented in the drawings are not necessarily to scale, emphasis instead being placed upon illustrating the principles of the invention. And, in the drawings, like reference numerals designate corresponding parts throughout the several views.

FIG. 7 depicts the device shown in a configuration for compressing fatty tissue.

FIG. 8 shows the block positioned partially underneath the fixed top portion after compression. The top is removed for illustrative purposes.

DETAILED DESCRIPTION OF PREFERRED EMBODIMENTS

Figure 1:
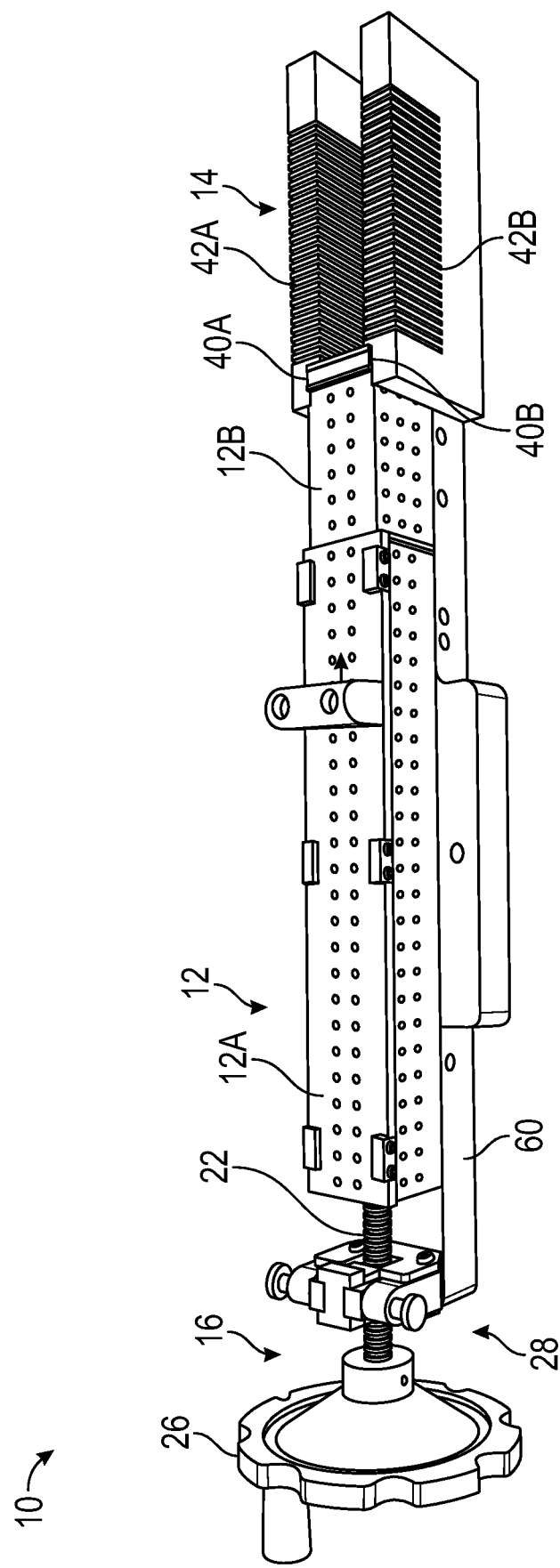
FIG. 1 depicts an exemplary device for yielding lymph nodes from fatty tissue shown in a configuration for cutting compressed tissue into sections for histopathological evaluation.

Among the benefits of the invention include devices and methods that substantially increase the yield of lymph nodes for tissue sections used for histopathological evaluation compared to manual palpation methods. Further, the tissue sections obtained using the devices and methods herein include total embedded material, which in addition to lymph nodes provides arteries, veins, nerves, connective tissue and other components for evaluation. At the same time, the devices and methods do not require the manual palpation of fatty tissue samples. Still further, the devices and methods substantially reduce the number of histology cassettes by 80%, 90%, 95% or more than would be required for complete analysis of total embedded material using methods currently used in the clinic.

As will be further described, the invention provides devices and methods, which uniformly and efficiently section total embedded material from fatty tissue samples for subsequent histopathological evaluation. It is expected that histopathological evaluation of total embedded material will become the new standard. Further, the sectioned samples are sized for use with histology cassettes, thereby avoiding a need to further size the sections for insertion into a histology cassette. As such, the devices and methods permit histological evaluation of all lymph nodes from resected tissue, and in addition, all of the surrounding biological components having potentially useful information, collectively referred to as "total embedded material." Still further, while the device and method are primarily described for clinical use for the treatment or staging of patients, they can also be used in research environments, such as to study the affect of cancer treatment.

The skilled artisan will appreciate that while the devices are depicted primarily with reference to manual use embodiments, the devices and methods can be modified by replacing manual actions with automation, such as by incorporating motors, sensors, automated cutters, sample transfer machinery and suitable software. As such, the invention also encompasses automated components and methods for compressing at least partially dissolved fatty tissue to form compressed tissue consisting essentially of total embedded material and cutting the compressed tissue into suitable sections for placement in histology cassettes.

For clarity of disclosure, and not by way of limitation, the invention is discussed according to different detailed embodiments; however, the skilled artisan would recognize that features of one embodiment can be combined with other embodiments and is therefore within the intended scope of the invention. Unless defined otherwise, all technical and scientific terms used have the same meaning as is commonly understood by one of ordinary skill in the art to which this invention belongs. If a definition set forth in this document is contrary to or otherwise inconsistent with a well-accepted definition set forth in the art, the definition set forth in this document prevails over a contradictory definition.

The term "complementary structures" as used herein refers to structures having surfaces configured to reversibly mate with one another to reversible lock components together. Examples of complementary structures include pin and aperture, clasps, tongue and groove, hook and loop (VELCRO) and others. The sample chamber and cutting chamber have complementary structures that permit connection and disconnection. Likewise, the sample chamber and gate preferably have complementary structures to permit the gate to open and lock closed.

The term "distal" or "distal end" as used herein refers to the region or end of the device or component that is furthest in relation to the direction that tissue is passed. Total embedded material exits the distal end of the sample chamber.

The term "entirely traverse the sample chamber" as used herein refers to the ability of the block to extend at least 99% of the length of the sample chamber. Preferably, the block is capable of extending beyond the distal end of the sample chamber when the gate is open to ensure passage of the entire compressed tissue into the cutting chamber for uniform sectioning.

The term "histological evaluation" or "histopathological evaluation" as used herein refers to evaluation of the microscopic structure of tissues in connection with disease, such as for staging of cancer. It is conventionally performed by thinly slicing sections for mounting on slides, which are then viewed optically.

The term "locked" as used herein refers to the ability of the gate to remain in its closed position while compressing tissue longitudinally against the gate.

The term "proximal" or "proximal end" as used herein refers the beginning region or end of the device or component in relation to the direction tissue is passed through the device. The proximal end of the cutting chamber connects to the distal end of the sample chamber.

The term "receiving ports are rotationally aligned" as used herein refers to the alignment of one port after another such that over a 360 degree rotation of a wheel each port has been aligned to receive compressed tissue from the sample chamber.

The term "sets of opposing through slots" as used herein refers to sets of two slots that are aligned on opposing sidewalls such that each set of two slots can be linearly traversed through the cutting chamber, such as to permit passage of a knife. Opposing through slots are preferably perpendicular to the direction that the compressed tissue passes through the cutting chamber.

The term "totally embedded material" or "total embedded material" as used herein refers to the biological components that remain when fatty tissue is eluted from a resected fatty tissue sample. Such biological components include lymph nodes, vessels, nerves, and/or connective tissue. Using the devices and methods, total embedded material is compressed into a substantially smaller tissue volume (e.g. from 100% to 10%), sectioned, and placed in cassettes for subsequent histopathological evaluation and thus staging of cancer. It is expected that histopathological evaluation of total embedded material will become the new standard, replacing the clinical guidelines of 12 lymph nodes for staging of cancer.

The term "opened" as used herein refers to removal of the gate from its closed position. An "opened" gate permits passage of compressed tissue out of the sample chamber and into a cutting chamber or receiving port.

Reference will now be made in detail to non-limiting embodiments of the present invention by way of reference to the accompanying drawings, where like reference numerals refer to like parts, components, and structures.

As an introduction, FIGS. 1-9 depict an exemplary device 10 for yielding lymph nodes from fatty tissue. The device 10 includes a fenestrated sample chamber 12, a cutting chamber 14, a pusher 16, and a lockable gate 18. Expanding on the introduction to the device 10 and method depicted in FIGS. 1-9, a sample of resected fatty tissue having lymph nodes is loaded into the sample chamber 12 and compressed against a closed gate 18 using the pusher 16, where dissolved fat and other fluids are pushed outward through fenestrations 20. The resulting compressed tissue, which is typically about 10% of the initial fatty tissue volume, is referred to as "total embedded material" due to its densely packed lymph nodes and other biological components, such as arteries, veins, nerves, and/or connective tissue. The gate 18 is opened and the compressed tissue, is pushed into the cutting chamber 14 where it is cut into sections pre-sized for placement in histology cassettes for further histopathological evaluation, such as for staging of cancer, such as during staging, treatment and prognosis of cancer.

The device 10 improves staging of various cancers by way of improving the yield of lymph nodes from fatty tissue resected from a location of a cancer, and thus the device 10 is suited to process lymph nodes from various locations of the body. The device 10 can process any fatty tissue sample for evaluation of lymph nodes and/or components such as arteries, veins, nerves and/or connective tissue. As non-limiting examples, the sample of fatty tissue can be resected tissue from regions nearby the colon, the stomach, the esophagus, the bladder, the pancreas and other regions where fatty tissue is suspected of having lymph nodes susceptible of metastasis. The fatty tissue can be resected from regions near a tumor.

Prior to loading fatty tissue into the sample chamber 12, preferably the fatty tissue is pretreated with a solvent that can at least partially but more preferably mostly dissolve the fatty tissue, thereby permitting the elution (wash-out) of fatty droplets (fat cells). By at least partially, and more preferably mostly, dissolving the fatty tissue, its removal during the compression step is improved, and the number of cassettes for histopathological evaluation of the embedded material can be reduced. Experimentally, it has been found that the device 10 reduces the number of required histology cassettes by about 90% or more compared to conventional processing of a same fatty tissue sample.

Fatty tissue is typically received in formalin or a formaldehyde-based fixing solution after resection. In preferred embodiments, the formalin solution is replaced with Carnoy's solution. In particular, it has been found that Carnoy's solution improves fatty tissue dissolution and thus improves the quality of tissue sections for histopathological evaluation. It is contemplated that other solvents based on mixtures of ethanol, chloroform and glacial acetic acid could also be used, although Carnoy's solution is currently preferred.

The sample chamber 12 is configured to receive the fatty tissue and therefore can vary in volume. However, the sample chamber 12 preferably has height and width dimensions so that after compression, the compressed tissue only requires cutting along its longitudinal length for placement in histology cassettes. That is, the width and height of the interior portion of the sample chamber 12 is preferably sized within the dimensions of a conventional histology cassette. In some embodiments, the width and height of the interior of the sample chamber 12 is about 1 or 2 mm smaller than that of the histology cassette used with the device 10. As general guidance the international standard for histology cassettes is about 22 mm by about 23 mm. As such, the preferred dimensions for such a cassette would be about 20-21 mm by about 21-22 mm, though smaller dimensions could also be used. By sizing the sample chamber 12 to conform to histology cassette sizing, further size adjustment of the compressed tissue is not required for loading into histology cassettes.

The sample chamber 12 is preferably formed from metal or metal alloy and is preferably configured as having two portions, which primarily differ by the top, namely, a removable top portion 12A and a fixed top portion 12B. The fixed top portion 12B is positioned distal to the removable top portion 12A so that as the fatty tissue is compressed, it compresses against the locked gate 18, fenestrated sidewalls and the fixed top portion 12B. By providing a removable top portion 12A separate from a fixed top portion 12B, the outward forces exerted by the compressed tissue can be selectively exerted against the fixed top portion 12B rather than the removable top portion 12A. The operator is therefore able to easily remove and reattach the removable top portion 12A to load additional sample while the fixed top portion 12B remains under pressure from compressed tissue. Further, the sample chamber 12 is preferably removably mounted to a base 60 as further support during use.

One of ordinary skill in the art to which the invention belongs would recognize that the length ratio of the removable top portion 12A to the fixed top portion 12B can vary; however, in preferred embodiments the length of the removable top portion 12A is significantly greater than the length of the fixed top portion 12B due to the reduction of sample volume during tissue compression. As general guidance, the device 10 and methods herein result in compressed tissue that is about 10% of the volume of the original fatty tissue sample when using Carnoy's solution.

Figure 2:
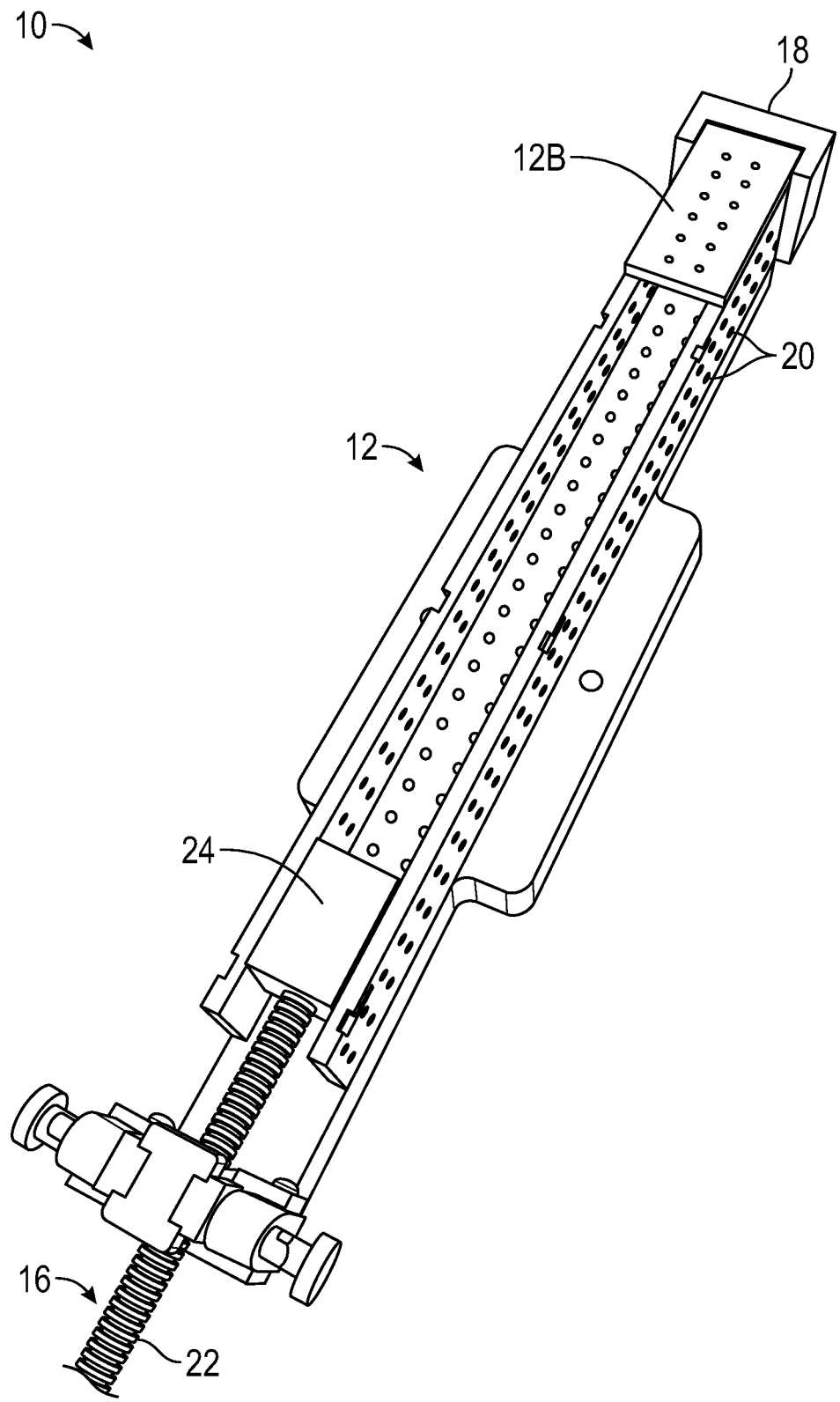
FIG. 2 depicts the device in a loading configuration for loading a sample of fatty tissue.

Turning to FIG. 2, the device 10 is shown in its sample loading configuration, which is characterized as having an open chamber 12 with retracted pusher 16. The fatty tissue is loaded distal to the pusher 16.

Figure 3:
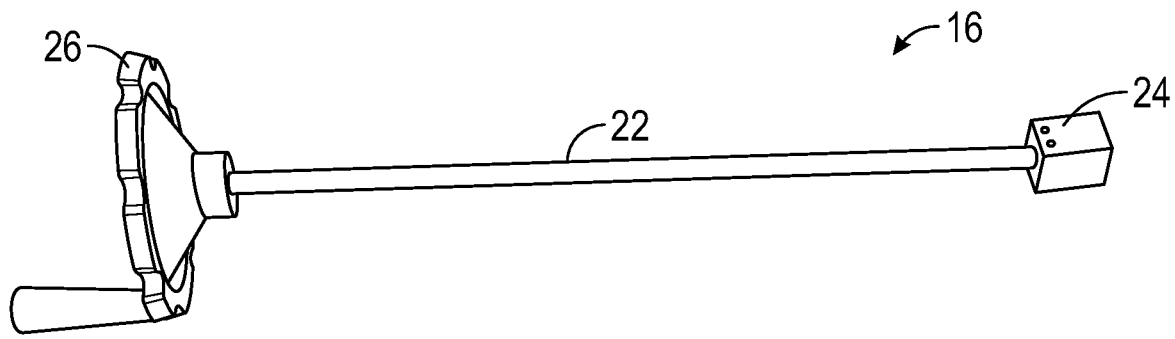
FIG. 3 depicts an exemplary pusher.

As shown in FIG. 3, the pusher 16 is preferably constructed as an elongated threaded rod 22, having at its distal end a block 24 and at its proximal end an actuator 26. Moving to FIG. 4, the threaded rod 22 exits the sample chamber 12 proximally and is fed through a guide 28.

Figure 4:
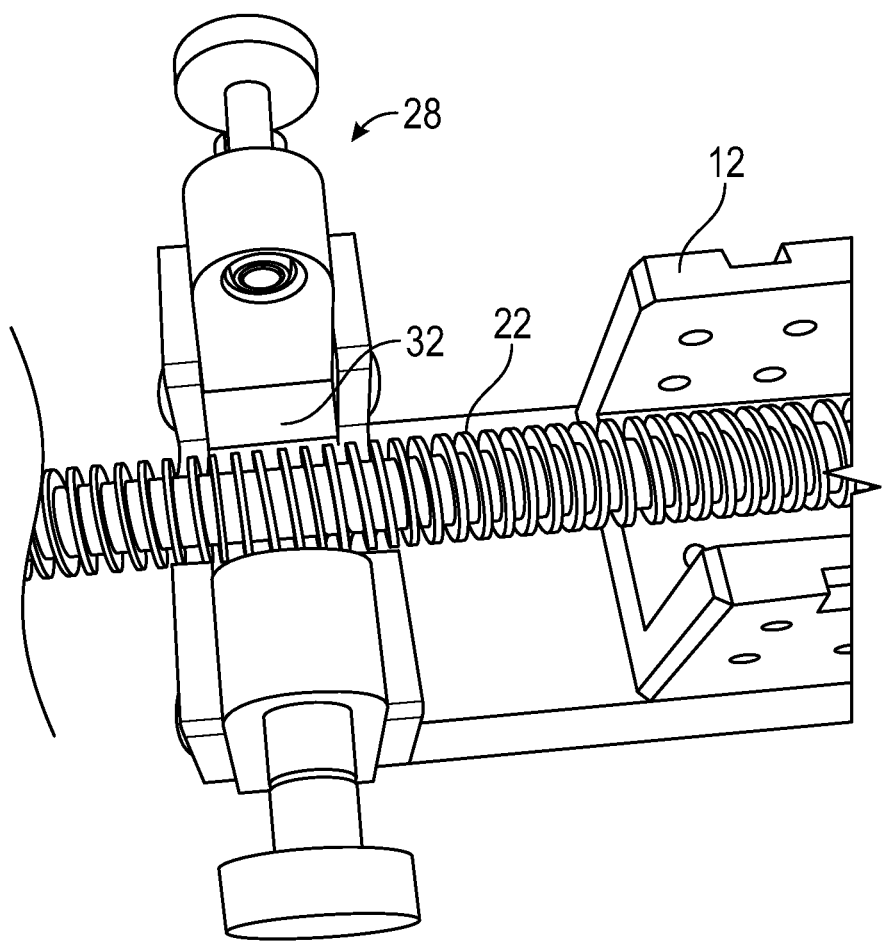
FIG. 4 depicts the guide configured to permit longitudinal sliding of the threaded rod.
Figure 5:
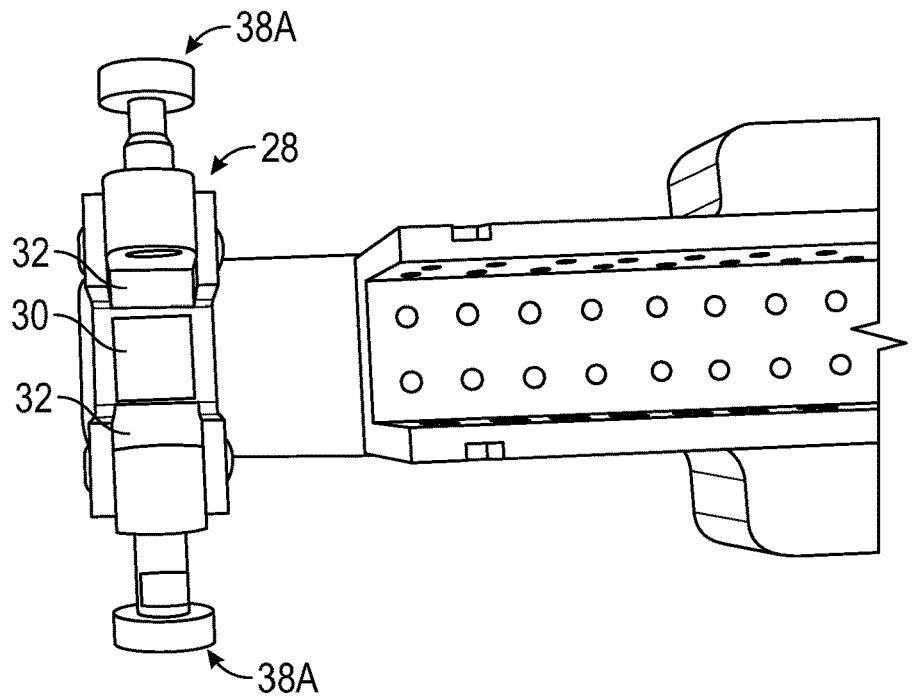
FIG. 5 depicts an exemplary smoothed bottom and inner sides of the guide.
Figure 6A:
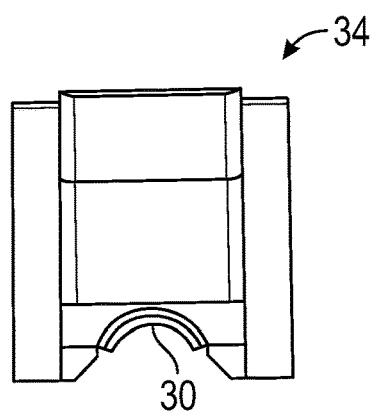
FIGS. 6A-C depict different views of an exemplary threaded top of the guide.
Figure 6B:
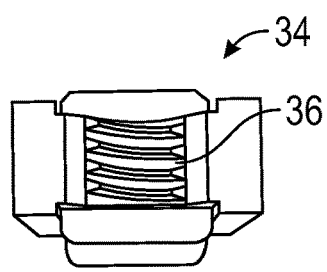
Figure 6C:
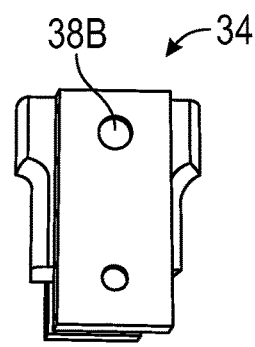
Figure 9:
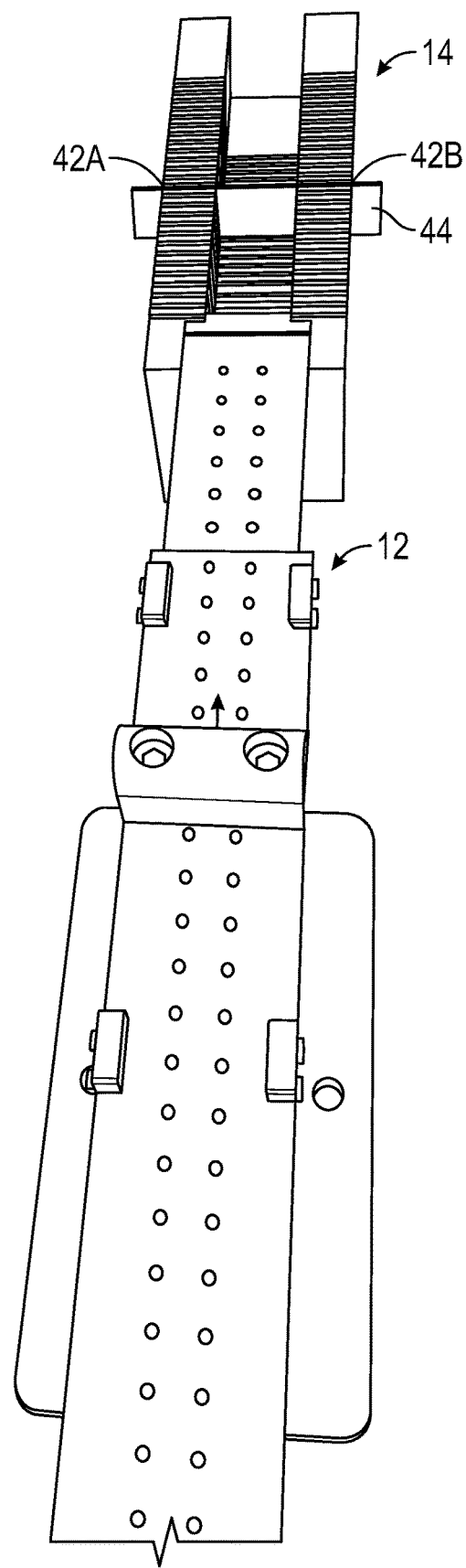
FIG. 9 depicts a barrier extending across a set of opposing through slots of the cutting chamber.

The guide 28 itself has two configurations. FIGS. 4 and 5 show a first configuration, where the guide 28 consists essentially of a smoothed bottom 30 and lateral sides 32 to permit the threaded rod 22 to slide longitudinally without requiring rotation. This configuration permits the operator to quickly pull the threaded rod 22 proximally, thereby permitting the loading of fatty tissue. With reference to FIGS. 6A-C and FIG. 7, a second configuration is characterized by the attachment of a threaded top 34 that has threads 36 complementary to the rod 22. When attached, the threaded top 34 engages the threads of the rod 22 for helical rotation. The threaded top 34 is preferably locked into threaded engagement with the rod 22 or unlocked for removal from threaded engagement with the rod 22 by way of complementary locking structures 38A, 38B on the guide 28, such as complementary pull pins and apertures. As shown better in FIG. 8, once engaged, rotation of the actuator 26 turns the threaded rod 22, which moves the block 24 longitudinally. This rotational configuration permits additional force to be applied manually during compression. To this end, the first configuration shown in FIG. 4 permits longitudinal sliding of the rod 22; whereas the second configuration shown in FIG. 7 requires rotation of the threaded rod 22 for longitudinal movement. While not shown, in some embodiments, the rod 22 is coupled to a motor for longitudinal movement in both proximal and distal directions.

As shown in more detail in FIG. 7 and FIG. 8, at the distal end of the sample chamber 12 is a lockable gate 18, which provides two functions. First, when locked in the closed position as shown in FIG. 7 and FIG. 8, it provides a distal surface against which the fatty tissue can be compressed. Second, when unlocked to the open position, such as by removal, the gate 18 permits passage of compressed tissue into the cutting chamber 14. In preferred embodiments, unlocking the gate 18 involves removing the gate 18 from the sample chamber 12. As such, preferably the gate 18 is configured to close a distal portion of the sample chamber 12 for compressing fatty tissue (see FIG. 7), and after compression is configured to open, thereby permitting passage of compressed tissue into the cutting chamber 14 (see FIG. 1). While the gate 18 can be provided in different forms, a preferred approach is to configure the gate 18 as an end cap, which slides downward and over the sample chamber 12 to its locked position, which terminally blocks the sample chamber 12 and is unlocked by pulling upwards for its removal to open the chamber 12. However, it is also envisioned that the gate 18 could be configured to slide horizontally to open and close. Most preferably the gate 18 slides along a same structure along an outside of the sample chamber 12 as the cutting chamber 14 slides; however, this is not required. For instance, while it is preferred to have both the gate 18 and the cutting chamber 14 configured to slide along a same set of grooves or ridges along the sample chamber 12, it is also envisioned that a second outer structure could also be used for selectively sliding the gate 18.

As yet another example, the sample chamber 12 could have an end slot to permit the gate 18 to slide vertically or horizontally into the sample chamber 12, thereby providing an insertable terminal surface. However, this configuration is not currently preferred.

Returning to FIG. 7, after adding fatty tissue to the sample chamber 12, the removable top portion 12A is locked into place, the threaded top 34 of the guide 28 is locked into threaded engagement with the rod 22, and the rod 22 is helically moved in the distal direction along the longitudinal axis of the sample chamber 12 to compress the fatty tissue against the gate 18 locked in its closed position. As shown more clearly in FIG. 8, longitudinal movement of the rod 22, moves the pusher 16 through the sample chamber 12 to push the fatty tissue distally (the removable top is removed for demonstration purposes).

Pushing the fatty tissue distally causes the tissue to press against the locked gate 18. Continuing to press the fatty tissue against the gate 18 expels or elutes dissolved fat, fixatives and any other solvents present in the fatty tissue sample from the fenestrations 20, which are typically sized about 0.5-5 millimeters. As the tissue is compressed, the sample volume that remains in the sample chamber 12 decreases by about 90%. Thus, after compression, the remaining 10% or so of tissue volume consists essentially of total embedded material. This total embedded material is characterized by a substantial increase in density of lymph nodes and other biological components, such as arteries, veins, nerves and connective tissue. The overall yield is consistently 100% or about 100% of the lymph nodes loaded from the fatty tissue. After tissue compression, the gate 18 is unlocked to its open position.

Turning back to FIG. 1, in preferred embodiments the cutting chamber 14 is configured for attachment to the sample chamber 12 by way of complementary engaging structures 40A, 40B, such as tongue and groove, clips, snaps, interference fit or others. Most preferably, both the gate 18 (FIG. 7) and the cutting chamber 14 (FIG. 1) attach to the sample chamber 12 at a same complementary structure 40A on the sample chamber 12 itself. In such configurations, the gate 18 is removed and the cutting chamber 14 attached. Although the invention is also intended to encompass embodiments where the cutting chamber 14 and sample chamber 12 are permanently fixed to one another.

Compressed tissue is pushed into the cutting chamber 14 using the pusher 16. Preferably, the pusher 16 has a sufficient length that the block 24 enters the cutting chamber 14 to at least the first set of opposing through slots 42A, 42B, which assists with complete sectioning of the compressed tissue.

Once pushed into the cutting chamber 14, the compressed tissue is preferably cut into uniformly thick sections. Uniform cutting is arranged by way of sets of opposing through slots 42A, 42B equally spaced and positioned along opposing sidewalls of the cutting chamber 14. Preferably, the cutting chamber 14 has an open top and the through slots 42A, 42B extend from the top to the bottom of the interior of the cutting chamber 14 to completely cut the compressed tissue into distinct sections. The sections are preferably cut into uniform sections of about 2.5 mm thick or less, which is sized for insertion into histology cassettes. As shown more clearly in FIG. 9, to further ensure uniformity across all sections and/or to improve tissue cutting at the distal end of the compressed tissue, the device 10 can also include a barrier 44 that can be removably inserted across a set of opposing through slots 42A, 42B. By abutting the barrier 44 against the distal end of the fatty tissue, further structural support can be provided while cutting, which can improve the quality of tissue sections, in particular, at the distal end.

Removing sectioned tissue from the cutting chamber 14 can be by continued displacement of the block 24 distally or can be by way of lifting the sectioned tissue away from the cutting chamber 14. In a preferred approach, the sectioned tissue is lifted outwards using a thin spatula configured to slide underneath the sectioned tissue. The sectioned tissue can then be placed in histology cassettes for further processing without additional sizing, thereby saving time by the operator.

The invention described may be embodied in other specific forms without departing from the spirit or essential characteristics thereof. The specific embodiments previously described are therefore to be considered as illustrative of, and not limiting, the scope of the invention.

Figure 10:
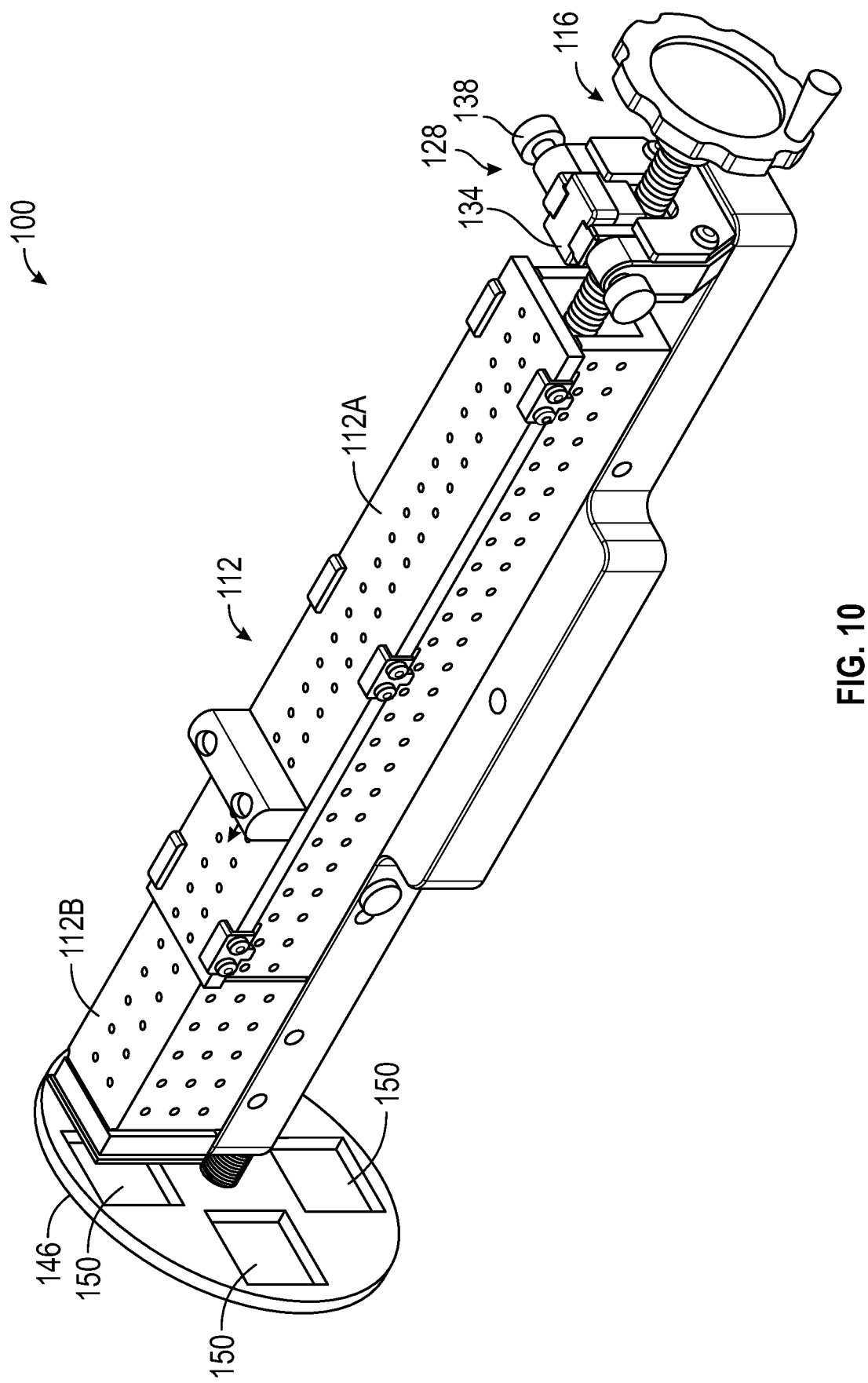
FIG. 10 depicts another exemplary device for yielding lymph nodes from fatty tissue.
Figure 11:
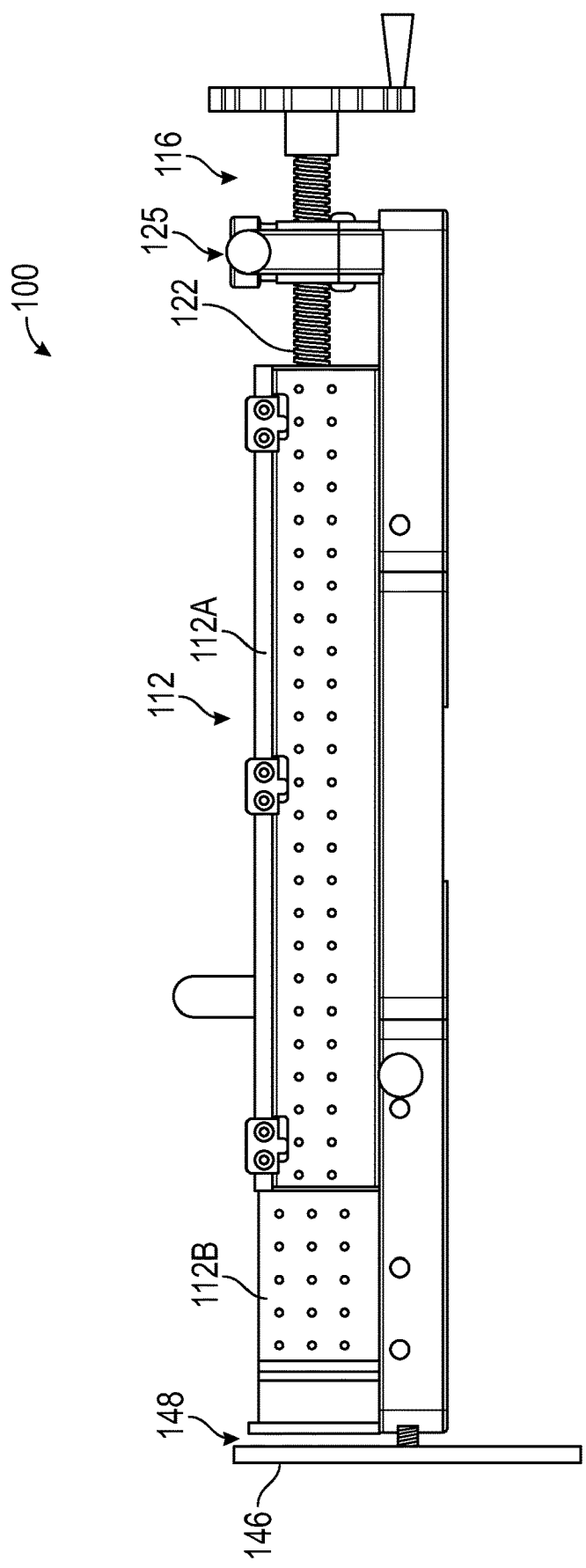
FIG. 11 is a side view of the device shown in FIG. 10.

As such, in a related aspect, FIG. 10 and FIG. 11 depict another exemplary device 100 for yielding lymph nodes from fatty tissue. The device 100 includes a fenestrated sample chamber 112 and a pusher 116 configured to move longitudinally through and entirely traverse the sample chamber 112. The device 100 also includes a wheel 146 spaced distal to the sample chamber 112 to form a cutting space 148 and is configured for rotation around a longitudinal axis of the sample chamber 112. The wheel 146 has a plurality of receiving ports 150 rotationally aligned to receive fatty tissue from the sample chamber 112 one after another; and a lockable gate (not shown but the same as gate 18 in FIG. 7) configured to provide a surface against which fatty tissue can be compressed and to regulate passage of compressed tissue into the receiving ports 150.

Like the configuration depicted in FIGS. 1-9, the device 100 shown in FIG. 10 and FIG. 11, has a sample chamber 112 with a removable top portion 112A to provide access to the interior of the chamber 112. The preferred mechanism for longitudinal movement of the pusher 116 through the sample chamber 112 and towards the wheel 146 is the same mechanism for longitudinal movement set forth in FIGS. 1-9, namely, the pusher 116 is preferably constructed as an elongated threaded rod 122 exiting the sample chamber 112 proximally and fed through a guide 128. Like the configuration shown in FIGS. 1-9, the preferred guide 128 has a smoothed bottom and lateral sides (not shown) to permit the threaded rod 122 to slide longitudinally when a threaded top 134 that is threaded complementary to the rod 122 is removed. The threaded top 134 is preferably locked into threaded engagement with the rod 122 and unlocked for removal by way of complementary locking structures 138 such as pull pins and apertures.

Use of the device 100 begins substantially as provided previously. Preferably a sample of fatty tissue is pretreated with a solvent that mostly dissolves fatty tissue, preferably Carnoy's solution. After adding the fatty tissue to the sample chamber 112, the removable top portion 112A is locked, the threaded top 134 of the guide 128 is locked into threaded engagement with the rod 122, the gate (not shown) is locked in the closed position, and the rod 122 is helically moved distally along the longitudinal axis of the sample chamber 112 to compress the fatty tissue against the gate, which remains locked in its closed position.

Continuing to press the fatty tissue sample against the gate expels solvent and elutes dissolved fat out the fenestrations 120 of the sample chamber 112. As the tissue is compressed, the remaining sample volume decreases and the density of embedded material increases. As such, the compressed tissue is characterized as lymph nodes and other total embedded material.

Once sufficiently compressed, the gate is unlocked to its open position. The compressed tissue is then pushed into a receiving port 150 of the wheel 146. The compressed tissue is then cut into uniformly thick sections by way of cutting proximate to the wheel 146. The wheel 146 rotates such that another receiving port 150 is aligned with the sample chamber 112, and the compressed tissue is further pressed distally into the newly aligned receiving port 150, then again cut. The wheel 146 is again rotated and the process repeated for a next receiving port 150. Tissue sections are then removed from the receiving ports 150 and place on histology cassettes.

What is claimed is:

1. A device for collecting lymph nodes from fatty tissue, the device comprising:
   a) a fenestrated sample chamber comprising a plurality of throughbores arranged to elute fluid from the sample chamber, the sample chamber configured to receive a sample of fatty tissue comprising lymph nodes;
   b) a lockable gate switchable between a closed position that is locked and an open position;
   c) a pusher configured to push the sample against the gate when locked in the closed position to more densely pack the tissue and configured to push the packed tissue out of the sample chamber when the gate is subsequently opened; and
   d) a cutting chamber aligned distal to the sample chamber for receiving the packed tissue from the sample chamber, the cutting chamber comprising sets of opposing through slots aligned to permit slicing of the packed tissue into sections, thereby collecting the lymph nodes from the fatty tissue.

2. The device of claim 1, wherein the sample chamber comprises a removable top portion.

3. The device of claim 2, wherein the sample chamber comprises a fixed top portion positioned distal to the removable top portion.

4. The device of claim 1, wherein the sample chamber and cutting chamber comprise complementary structures that reversibly attach to one another, thereby permitting the cutting chamber to reversibly connect to the sample chamber.

5. The device of claim 1, wherein the pusher comprises a block and a threaded rod, the device further comprising a guide proximal to the sample chamber that longitudinally guides the threaded rod.

6. The device of claim 5, wherein the guide comprises a removable threaded top that engages the threaded rod.

7. The device of claim 6, wherein the guide comprises a bottom and sides that are not threaded.

8. The device of claim 1, wherein the gate is an end cap that reversibly caps the distal end of the sample chamber when the cutting chamber is not connected.

9. The device of claim 1, wherein the device further comprises a moveable support that fits within a pair of opposing through slots to traverse the cutting chamber.

10. A method of sectioning tissue into uniform sections for histology cassettes, the method comprising:
    a) providing the device of claim 1;
    b) adding a sample of fatty tissue comprising lymph nodes to the sample chamber;
    c) locking the gate in the closed position;
    d) pushing the fatty tissue against the gate to pack the tissue;
    e) opening the gate;
    f) pushing the packed tissue between the sets of opposing through slots; and
    g) cutting the packed tissue through the sets of opposing through slots to form a plurality of packed tissue sections sized for placement in histology cassettes.

11. The method of claim 10, wherein before the step of adding the sample of fatty tissue to the sample chamber, the method further comprises pretreating the sample with a solvent that at least partially dissolves fat.

12. The method of claim 10, wherein before the step of cutting the packed tissue, the method further comprises positioning a support across a set of opposing through slots of the cutting chamber and abutting a distal end of the packed tissue, thereby providing a distal support for the packed tissue during cutting.

13. The device of claim 1, wherein the cutting chamber is aligned distal to the gate.

14. A device for collecting lymph nodes from fatty tissue, the device comprising:
    a) a fenestrated sample chamber comprising a plurality of throughbores arranged to elute fluid from the sample chamber, the sample chamber configured to receive a sample of fatty tissue comprising lymph nodes;
    b) a lockable gate switchable between a closed position that is locked and an open position;
    c) a pusher configured to push the sample against the gate when locked in the closed position to more densely pack the tissue and configured to push the packed tissue out of the sample chamber when the gate is subsequently opened; and
    d) a wheel spaced distal to the sample chamber to form a cutting space and configured for rotation around a longitudinal axis of the sample chamber, the wheel comprising one or more receiving ports rotationally aligned to receive the packed tissue from the sample chamber in series.

15. The device of claim 14, wherein the one or more receiving ports comprise three or four receiving ports.

16. A method of sectioning tissue into uniform sections for histology cassettes, the method comprising:
    a) providing the device of claim 15;
    b) adding a sample of fatty tissue comprising lymph nodes to the sample chamber;
    c) locking the gate in the closed position;
    d) pressing the fatty tissue against the gate to pack the tissue;
    e) opening the gate;
    f) pushing the packed tissue into a first receiving port using the pusher;
    g) cutting the packed tissue within the cutting space to form a tissue section sized for placement in a histology cassette;
    h) rotating the wheel to align a second receiving port with the sample chamber;
    i) pushing the packed tissue into the second receiving port using the pusher;
    j) cutting the packed tissue within the cutting space to form a second tissue section sized for placement in a histology cassette; and
    k) optionally removing the cut tissue sections from the wheel.

17. The device of claim 14, wherein the cutting chamber is aligned distal to the gate.

18. A method of sectioning tissue for histology cassettes, the method comprising:
    a) providing a device for collecting lymph nodes from fatty tissue, the device comprising:
       a fenestrated sample chamber comprising a plurality of throughbores arranged to elute fluid from the sample chamber, the sample chamber configured to receive a sample of fatty tissue comprising lymph nodes,
       a lockable gate switchable between a closed position that is locked and an open position, thereby closing and opening the sample chamber at the gate, and a pusher configured to push the sample against the gate when locked in the closed position to more densely pack the tissue and configured to push the packed tissue out of the sample chamber when the gate is subsequently opened;
b) adding a sample of fatty tissue comprising lymph nodes to the sample chamber;
c) locking the gate in the closed position;
d) pushing the fatty tissue with the pusher to elute fluid through the throughbores and to pack the tissue;
e) opening the gate;
f) pushing the packed tissue from the sample chamber; and
g) cutting the packed tissue to form a plurality of packed tissue sections sized for placement in histology cassettes.

* * * * *